United States Patent
Popescu

(10) Patent No.: US 6,507,639 B1
(45) Date of Patent: Jan. 14, 2003

(54) METHOD AND APPARATUS FOR MODULATING THE RADIATION DOSE FROM X-RAY TUBE

(75) Inventor: Stefan Popescu, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/945,521

(22) Filed: Aug. 30, 2001

(51) Int. Cl.$^7$ .............................. A61B 6/00; H05G 1/44
(52) U.S. Cl. ..................... 378/108; 378/16; 378/145; 378/97
(58) Field of Search ..................... 378/16, 108, 109, 378/110, 145, 97

(56) References Cited

U.S. PATENT DOCUMENTS

| | | | | |
|---|---|---|---|---|
| 5,008,915 A | * | 4/1991 | Vlasbloem | 378/108 |
| 5,379,333 A | | 1/1995 | Toth | 378/16 |
| 5,400,378 A | * | 3/1995 | Toth | 378/108 |
| 5,450,462 A | * | 9/1995 | Toth et al. | 378/16 |
| 5,485,494 A | * | 1/1996 | Williams et al. | 378/110 |
| 5,625,662 A | | 4/1997 | Toth et al. | 778/108 |
| 5,696,807 A | | 12/1997 | Hsieh | 378/10 |
| 5,764,721 A | | 6/1998 | Light et al. | 378/16 |
| 5,822,393 A | | 10/1998 | Popescu | 378/108 |
| 5,867,555 A | | 2/1999 | Popescu et al. | 378/16 |
| 6,385,280 B1 | * | 5/2002 | Bittl et al. | 378/16 |

FOREIGN PATENT DOCUMENTS

| | | |
|---|---|---|
| DE | 199 57 083 | 6/2001 |
| DE | 199 57 082 | 8/2001 |

* cited by examiner

*Primary Examiner*—Drew A. Dunn
(74) *Attorney, Agent, or Firm*—Schiff Hardin & Waite

(57) ABSTRACT

In a method for modulating a radiation dose from an x-ray tube, and in an x-ray tube-containing apparatus, the x-ray tube has at least one variable operating parameter which, when varied, modulates the radiation dose, with a modulation speed, for x-rays produced by the x-ray tube, and the x-ray tube is operated while varying this parameter through a parameter range to generate modulation speed data, representing modulation speeds of the x-ray tube respectively for different values of the operating parameter. When an examination subject is to be irradiated with an x-ray dose from the x-ray tube, an exposure effect associated with the exposure of the subject to the radiation dose is identified, this exposure effect being dependent on modulation of the radiation dose. When exposing the subject to the radiation dose, the operating parameter is varied in advance of a time at which the exposure effect is to be achieved, dependent on the modulation speed data, so that the radiation dose is modulated to produce the desired exposure effect at the desired time.

18 Claims, 11 Drawing Sheets

METHOD AND APPARATUS FOR MODULATING THE RADIATION DOSE FROM X-RAY TUBE

BACKGROUND OF THE INVENTION

1. Field of the Invention

The present invention is directed to a method and apparatus for modulating the radiation dose from an x-ray tube, and in particular to such a method and apparatus for modulating the radiation dose to achieve a predetermined effect or result associated with the radiation dose.

2. Description of the Prior Art and Related Applications

Computed tomography (CT) is recognized as a diagnostic procedure employing x-rays emitted from an x-ray tube with a relatively high dose. This means measures must be taken to maintain the exposure to radiation, to which the patient and attending personnel are subjected, to levels which do not represent a radiation hazard. With the introduction of spiral (helical) CT and multi-slice volume scanning techniques, new examination procedures have become available. The primary advantages of these new scanning techniques, such as section-to-section continuity, detection of small lesions, and rapid acquisition of data, have produced an increase in the number of patients which can be examined within a given time period, and thus have also produced an increase in the average dose per individual of the population. According to recent legislation (e.g. Council Directive 97/43/ EURATON 1997) all doses due to medical exposure for radiological purposes, except for radiological therapeutic procedures, must be kept as low as is reasonably achievable. Dose reduction for CT purposes is strongly recommended and supported by the relevant national and international regulating authorities.

In accordance with these desires, scanning techniques are beginning to be employed in the field of CT wherein the x-ray level is adjusted dynamically during a scan. For this purpose, modulation of the radiation dose must be undertaken during the course of a scan. Dose modulation can be accomplished by adjusting the x-ray intensity during the rotation of the gantry of a CT apparatus, as a function of the gantry rotation angle and dependent on the instantaneous patient x-ray absorption at each particular tube angle position. Such techniques are described, for example, in U. S. Pat. Nos. 5,822,393 and 5,867,555 and 5,379,333. It is also known to modulate the x-ray dose dependent on the scanned body region by automatically adjusting the x-ray level during a longer spiral scan by making a compromise between the requirements for image quality and the applied dose, as described in U.S. Pat. Nos. 5,764,721 and 5,696,807 and 5,625,662.

It is also known to dynamically adjust the x-ray intensity during a scan dependent on the physiological condition of the organ under examination, such as the phase of a heart cycle in the case of cardio-dynamic scans, as described in German Application 19957083.3, corresponding to co-pending U.S. application Ser. No. 09/724,055 filed Nov. 28, 2000, and German Application P19957082.5, corresponding to co-pending U.S. application Ser. No. 09/724, 057, filed Nov. 28, 2000. It is also known to dynamically adjust the x-ray intensity during gantry rotation as a function of the tube angle in order to protect the eyes of the patient in the case of a head scan, or to protect the physician's hands in a biopsy scan, as described in the aforementioned U.S. Pat. Nos. 5,764,721 and 5,696,807 and 5,625,662.

None of the above-identified known techniques, however, adequately addresses the practical problem of the dose modulation speed which is available with conventional x-ray tubes. As described in U.S. Pat. No. 5,625,662, dose modulation is achieved in an x-ray tube used in a CT apparatus by modulating the tube current. The tube current modulation is, in turn, indirectly achieved by modulating the heating current supplied to the tube filament. Because of this, conventional x-ray tubes do not react fast enough to modulate the dose dependent on the instantaneous patient absorption during gantry rotation at fast speed. The failure to reproduce radiation peaks where the patient absorption is maximum increases the quantum noise in the measured signal, and significantly degrades the image quality.

The slow reaction of x-ray tubes to rapid changes in x-ray intensity is due to physical limitations in the filament structure, as well as the thermal inertia of the filament.

It is known from U.S. Pat. No. 5,822,393 that higher modulation speeds may be achieved using specially designed x-ray tubes, which have voltage-controlled gate electrode. This is a relatively expensive approach, however, and increases the complexity and cost of the x-ray tube and the associated electronics. It is known from the aforementioned U.S. Pat. No. 5,379,333, and co-pending U.S. application Ser. No. 09/376,361, filed Aug. 6, 1999, to artificially limit the modulation curve shape to a sinusoidally shaped template and to artificially limit the modulation index to a maximum of 50%. This approach is compatible with existing CT systems, but fails to achieve the maximum possible dose reduction because of the artificial limitation of the modulation index to 50%. Moreover, the sinusoidal template does not always match the peaks in the patient absorption profile, particularly in abdominal scans. Moreover, this technique does not achieve the maximum dose reduction, or satisfy requirements of other modulation techniques such as cardio-dynamic scans.

Another known technique is described in the article "Dose Reduction in CT by Anatomically Adapted Tube Current Modulation, II. Phantom Measurements," Kalender et al., Med. Phys., Vol. 26 (1999) pp. 2248-2253 to artificially limit the modulation index dependent only on the gantry rotation speed, for example, a maximum of 90% at 2 sec/rot to a maximum of 60% at 0.75 sec/rot. This known method, however, ignores the dependence of the modulation speed on the nominal tube current and on the focus size, and also is unable to achieve the maximum dose saving with conventional tubes.

Another known technique suggests the use of a pulsed x-ray tube with the x-ray pulse duration being adjusted to patient absorption. This technique, however, has a poor compatibility with the actual angle in angle triggered systems, and with time-triggered CT systems which use an integration period on the order of a few hundreds of microseconds. This technique also imposes significant requirements on the data measurement system. Moreover, the complete switching off of the x-rays during the pulse pauses may not be supported by all other sub-systems of a CT system, or may not be desired, such as in the case of cardio-dynamic scans.

All of the above-described known methods involve calculation of an initial x-ray profile which is desired to be achieved during a scan. An operating parameter of the x-ray tube, such as the tube current, is then varied during the scan in an effort to cause the x-ray tube to reproduce the desired x-ray profile. A conventional x-ray tube, however, as noted above cannot reproduce this profile because of its limited dynamic capabilities.

SUMMARY OF THE INVENTION

It is an object of the present invention to provide a method and an apparatus for modulating the radiation dose from an x-ray tube which allows a predetermined exposure effect, such as an x-ray profile, to be achieved using a conventional x-ray tube.

A further object is to provide such a method and apparatus wherein maximum dose reduction at target pixel noise is achieved by modulating the tube current in a conventional x-ray tube.

The above objects are achieved in accordance with the principles of the present invention in a method and an x-ray tube-containing apparatus, such as a computed tomography apparatus, wherein the x-ray tube has at least one variable operating parameter which, when varied, modulates the radiation dose, with a modulation speed, for x-rays produced by the x-ray tube, and wherein the x-ray tube is operated while varying the aforementioned parameter through a parameter range to generate modulation speed data, representing modulation speeds of the x-ray tube respectively for different values of the operating parameter. When an examination subject is to be subjected to an x-ray dose from the x-ray tube, an exposure effect associated with the exposure of the subject to the radiation dose is identified, this exposure effect being dependent on modulation of the radiation dose. When exposing the subject to the radiation dose from the x-ray tube, the operating parameter is varied in advance of a time at which the aforementioned exposure effect is to be achieved, according to the modulation speed data, so that the radiation dose is modulated to produce the desired exposure effect at the desired time.

The modulation speed of the x-ray tube can be measured during factory calibration procedures, and can be stored in computer tables as a function of the operating parameter. The tube's modulation speed, moreover, can be identified as a function of multiple operating parameters. The measurements are performed at defined points over the entire operating range of the x-ray tube. When a patient is being exposed to a radiation dose from the x-ray tube, a dose modulation unit calculates the actual modulation speed by multi-point interpolation, using the information stored in the table. The dose modulation unit then corrects the ideal, initial modulation profile before supplying it to the tube current modulation unit of the apparatus. The actual modulation speed is updated at fixed periods during the exposure, such as twice per rotation in a CT apparatus, and is used to correct the modulation profile so that the maximum (nominal) x-ray intensity is reached for those exposures wherein maximum x-ray intensity and minimum quantum noise are desired. The dose modulation unit anticipates the x-ray peaks thereby increasing the temperature of the tube filament, and thus also increases the tube current, at an earlier time than would occur in the conventional methods described above. The maximum speed which is actually available can thereby be taken advantage of, to achieve a maximum dose saving (reduction) and a target (lower) pixel noise, despite the slow speed of conventional x-ray tubes.

The invention is based on investigations which have demonstrated that the modulation speed of conventional x-ray tubes is a tube parameter that behaves differently dependent on the gradient direction of the x-ray profile as well as on the operating parameters of the x-ray tube. This investigation has identified those operating parameters which particularly influence the modulation speed.

This investigation has also demonstrated that only the rising portion of the modulation speed profile changes with tube operating parameters. The speed of the rising gradient depends on tube operating parameters such as the maximum tube current which is to be reached, the modulation index and the size of the focus (in a multi-filament tube). Therefore, in accordance with the invention dedicated tables are measured and stored to provide the modulation speed as a function of the tube current to be reached, the modulation index (minimum tube current in the scan) and the focus size. The aforementioned investigations have determined that the modulation speed does not depend on the magnitude of the high voltage that is applied to the tube.

The aforementioned investigations have shown that if the rising gradient of the dose modulation profile is not corrected to take into account the actual modulation speed, the x-ray intensity does not reach the peaks (maximum intensity) at the desired time. Therefore, in a CT apparatus the projections subject to maximum absorption are not exposed enough, and higher quantum noise will degrade the reconstructed image. To avoid this result, the inventive method calculates the actual modulation speed based on scan parameters and corrects the rising gradients within the initial modulation profile so that the actually employed x-ray profile is always above the initial calculated profile. This means that in any projection the quantum is ensured to be lower than the maximum expected, but at the same time the maximum dose reduction is achieved at the target pixel noise with available conventional tubes.

The aforementioned investigation has also demonstrated that the falling gradient of the tube response is not dependent on the operating parameters, but is an exponential decay with a time constant that depends exclusively on the thermal cooling constant of the heating filament of the tube. This means that for a given type of tube, the falling gradient is invariant. Therefore, in accordance with the invention, the falling gradient of the modulation of profile does not have to be pre-corrected. If the actual falling gradient produced by the tube is lower than the prescribed profile shape, then the x-ray level will be higher than necessary for the target noise. This may increase the total dose, but will not increase the noise in the final image. Nevertheless, the dose reduction is still the maximum that can be achieved for the target pixel noise with a slow x-ray tube (i.e., an x-ray tube having a slow cooling filament).

DESCRIPTION OF THE PREFERRED EMBODIMENTS

Figure 1:
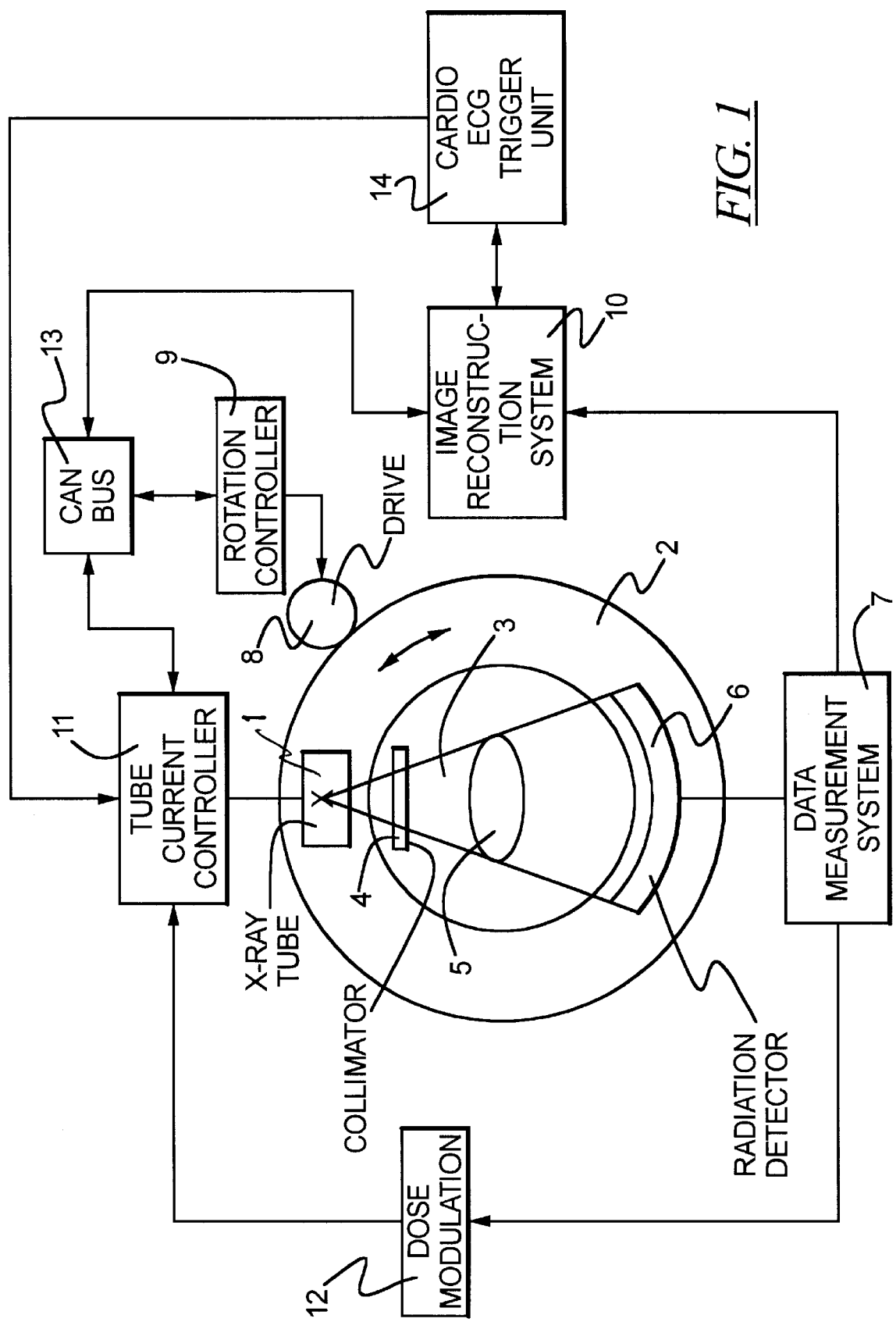
FIG. 1 is a schematic block diagram of a computed tomography apparatus constructed and operating in accordance with the principles of the present invention.
Figure 2:
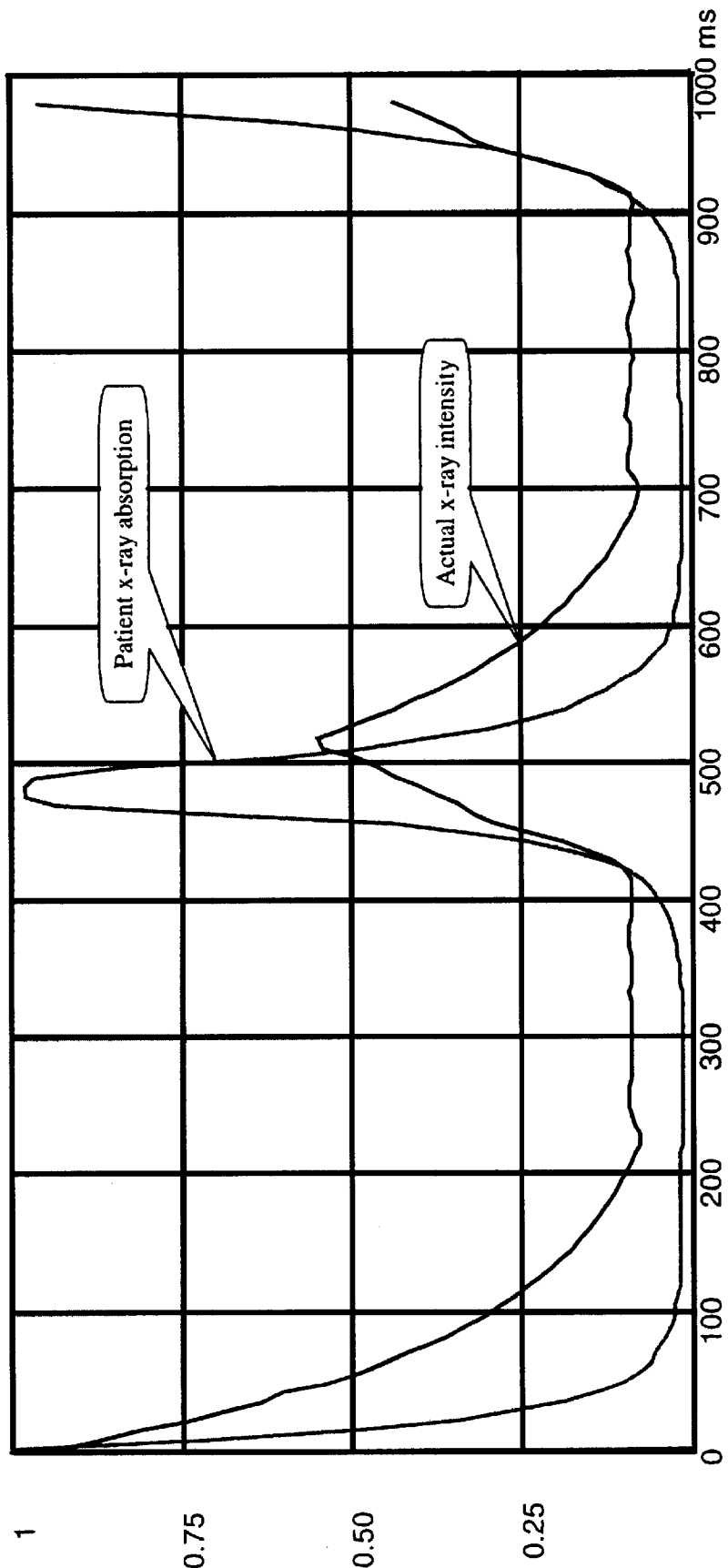
FIG. 2 illustrates the mis-alignment between the patient maximum x-ray absorption and the x-ray intensity peak as occurs in the conventional operation of a conventional x-ray tube.

FIG. 1 shows the basic components of a computed tomography system operating in accordance with the invention. The computed tomography system has an x-ray tube 1 which is mounted on a rotatable gantry 2 together with a radiation detector 6. The x-ray tube 1 is operated by a tube current controller 11 to emit an x-ray beam 3, which irradiates an examination subject 5. The x-ray beam 3 can be gated by a collimator 4.

X-rays attenuated by the examination subject 5 strike the radiation detector 6 and are recorded in a data measurement system 7. While the examination subject 5 is being irradiated with x-rays, the gantry 2 is rotated by a drive 8 so that the patient is irradiated with the x-ray beam 3 from a number of different projection angles. The data measurement system therefore records a number of projection datasets, which are supplied to an image reconstruction system 10. The image reconstruction system 10 generates an image of an interior slice of the examination subject 5 in a known manner from the projection datasets, and displays it at a monitor which is a part of the image reconstruction system 10.

For cardio-scans, activation of the x-ray tube 1 can be controlled by cardio ECG trigger unit 14 which, although not shown in FIG. 1, is connected in a known manner to obtain an ECG signal from the examination subject 5. The cardio ECG trigger unit, based on the ECG signal, supplies a control signal to the tube current control 11 which, in turn, activates the x-ray tube 1 at predetermined points in time during the cardiac cycle.

The drive 8 is operated by a rotation controller 9 to rotate the gantry 2 at a speed selected dependent on examination parameters. The tube controller 11, the rotation controller 9 and the image reconstruction system 10 all communicate with each other via a bi-directional CAN bus 13.

The computed tomography apparatus of FIG. 1 also includes a dose modulation unit 12 which has a table stored therein containing previously-determined data representing the modulation speed of the x-ray tube 1 dependent on one or more operating parameters. The dose modulation unit 12 is connected to the tube current controller 11 and supplies a profile thereto for operating the x-ray tube 1, which takes the modulation speed of the x-ray tube 1 into account so that an exposure effect, which is dependent on the type of examination being undertaken, can occur at the desired time, without a time lag due to the slow modulation speed of the x-ray tube 1. Some examples of the different types of exposure effect which can be achieved are as follows.

Figure 3:
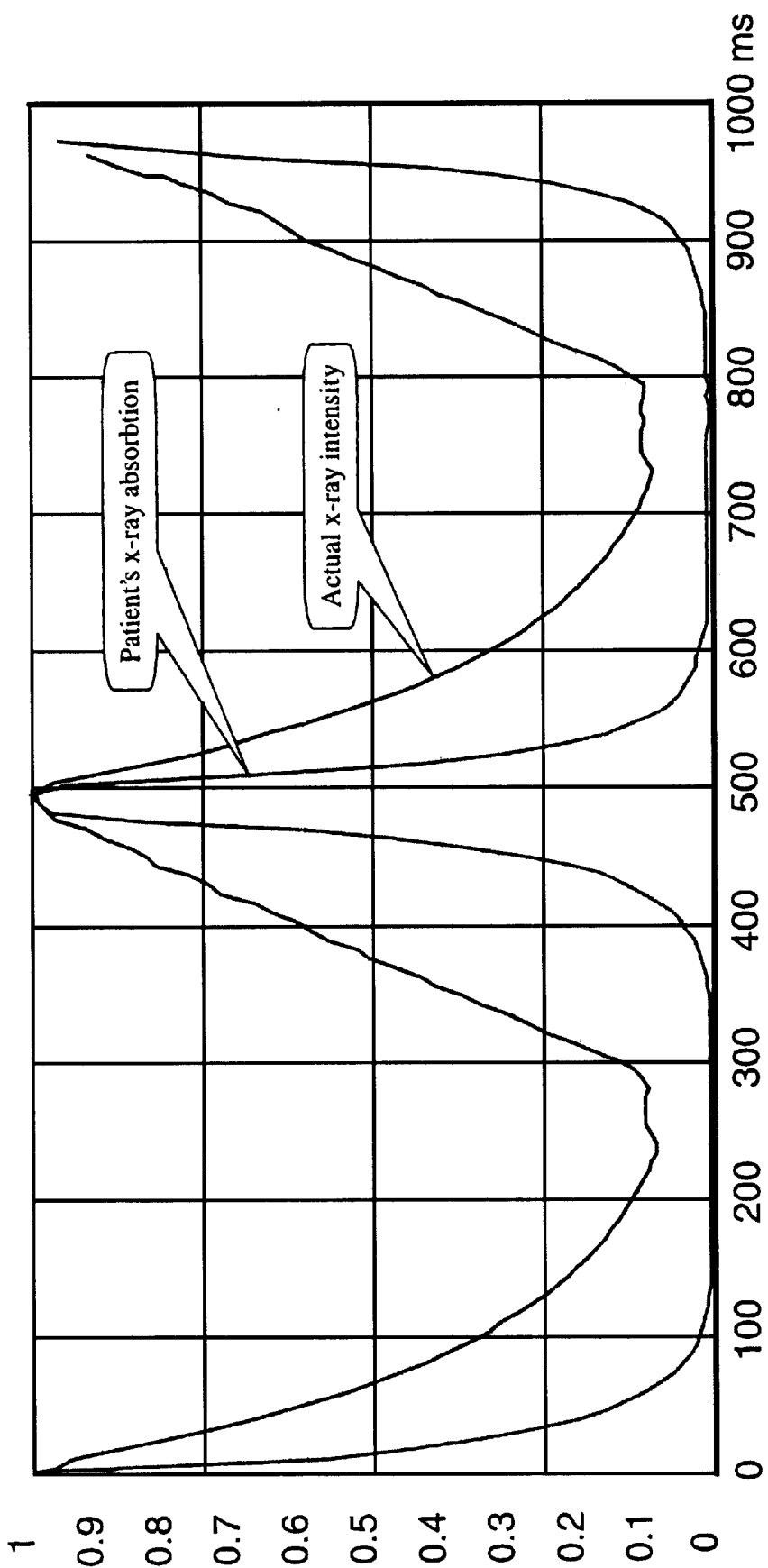
FIG. 3 illustrates the close alignment of the patient's maximum x-ray absorption and the x-ray intensity peak achieved in accordance with the invention.

Dose modulation during gantry rotation can be adapted to the patient anatomy in an improved manner compared to the basic method disclosed in the aforementioned U.S. Pat. No. 5,867,555 by the dose modulation unit 12 receiving patient absorption data from the data measurement system 7, and calculating a dose modulation profile for the next rotation of the gantry 2. As described above, the fast-rising gradients within the initial profile are pre-corrected dependent on the stored modulation speed data before the finalized profile is supplied to the tube current controller 11. In this manner the tube current is increased slowly at a time that is earlier than would occur using the uncorrected profile (as in the prior art) so as to ensure that the maximum patient x-ray absorption will substantially coincide with the peak value of the x-ray intensity, as shown in FIG. 3.

Dose modulation can also be undertaken during rotation using predefined templates. In this case, a predefined dose profile, such as a trapezoid or a sinusoidal profile, is supplied to the tube current controller 11. Unlike the earlier described conventional methods, wherein the modulation index is limited to 50% in order to accommodate the slow speed of the x-ray tube 1, in the inventive method the maximum dose savings can be achieved because it is not necessary to limit the modulation index. The faster rising gradients are pre-corrected in an optimum manner dependent on the actual speed that is calculated based on scan parameters.

Dose modulation also can take place in a synchronized manner with regard to bio-mechanical movements within the body of the examination subject 5, such as respiration or heartbeats, in the case of cardio-scans. In certain types of CT scans, the movement of the body disturbs the scanning process and the acquired data may not be suitable for reconstruction within certain periods when the motion artifacts are too high. To reduce the total radiation dose to the patient, the radiation level must be reduced until the target organ is again in a rest condition. As described above, in conventional methods for this purpose, a dedicated unit calculates the times at which the radiation dose should be increased to maximum levels. In the inventive method, the cardio ECG trigger unit 14 transmits CAN commands directly to the tune current controller 11 to update the x-ray intensity. Furthermore, based on the operating parameters of the x-ray tube 1, the cardio ECG trigger unit 14 shifts the commands forward in time to set the x-ray intensity so that even a slow speed conventional x-ray tube 1 will reach the intended intensity not later than desired. For this purpose, the aforementioned previously obtained data tables representing the modulation speed as a function of one or more parameters can be duplicatively stored in the cardio ECG trigger unit 14, or the cardio ECG trigger unit 14 can have access to the tables stored in the dose modulation unit 12. Another alternative is to store the table in a separate memory, accessible by both the cardio ECG trigger unit 14 and the dose modulation unit 12.

The dose modulation can also be undertaken dependent on the rotational angle of the gantry 2, by reducing the radiation dose level for certain projection angles and increasing it for other projection angles. This takes place based on CAN commands sent from the rotation controller 9 directly to the tube current controller 11 via the CAN bus 13. This type of dose modulation may be suitable for biopsy scans of head scans, so that the radiation level that would otherwise be directly incident on the eyes of the examination subject 5 or the hands of the attending physician. The CAN commands produced in accordance with the inventive method are shifted forward in time, dependent on the operating parameters of the x-ray tube 1, to take into account the modulation speed of the x-ray tube so that the x-ray tube 1 reaches the intended x-ray intensity not later than intended.

In developing the inventive method and apparatus, investigations were undertaken to determine the relationship between the modulation speed of an x-ray tube and various operating parameters thereof. FIGS. 4A through 8 illustrate some of the relationships which were determined in the course of these investigations. For this purpose, a P20 x-ray tube generator ensemble was employed, and the modulation speed thereof, expressed in mA/ms, was measured in the dose modulation mode for various nominal tube currents, for various modulation index (HUB) values, and for a large focus and a small focus. The speed was found to vary between 0.8 and 5 mA/ms, dependent on scan parameters such as nominal dose and modulation index. Even for the same focus size, the modulation speed covers a range between 1 and 5 mA/ms. This is a factor of 5 in the dose reduction, dependent on the scan parameters and not on the patient-slice absorption profile. Nevertheless, for the same nominal dose, there is a factor larger than 2 in modulation speed reduction depending on the modulation index.

The modulation speed achieved by the P20 x-ray radiator depends on the nominal dose and is significantly slower for a lower dose. The modulation speed decreases substantially linearly with nominal tube current from a maximum value obtained at 500 mA nominal. This is an unfavorable effect for the dose modulation mode, because the reduced modulation speed means losses in the dose saving, and an unnecessary dose applied to the examination subject 5, particularly for faster rotation speeds. The dose saving in the modulation mode increases as the nominal dose decreases for the same slice-patient.

Figure 4A:
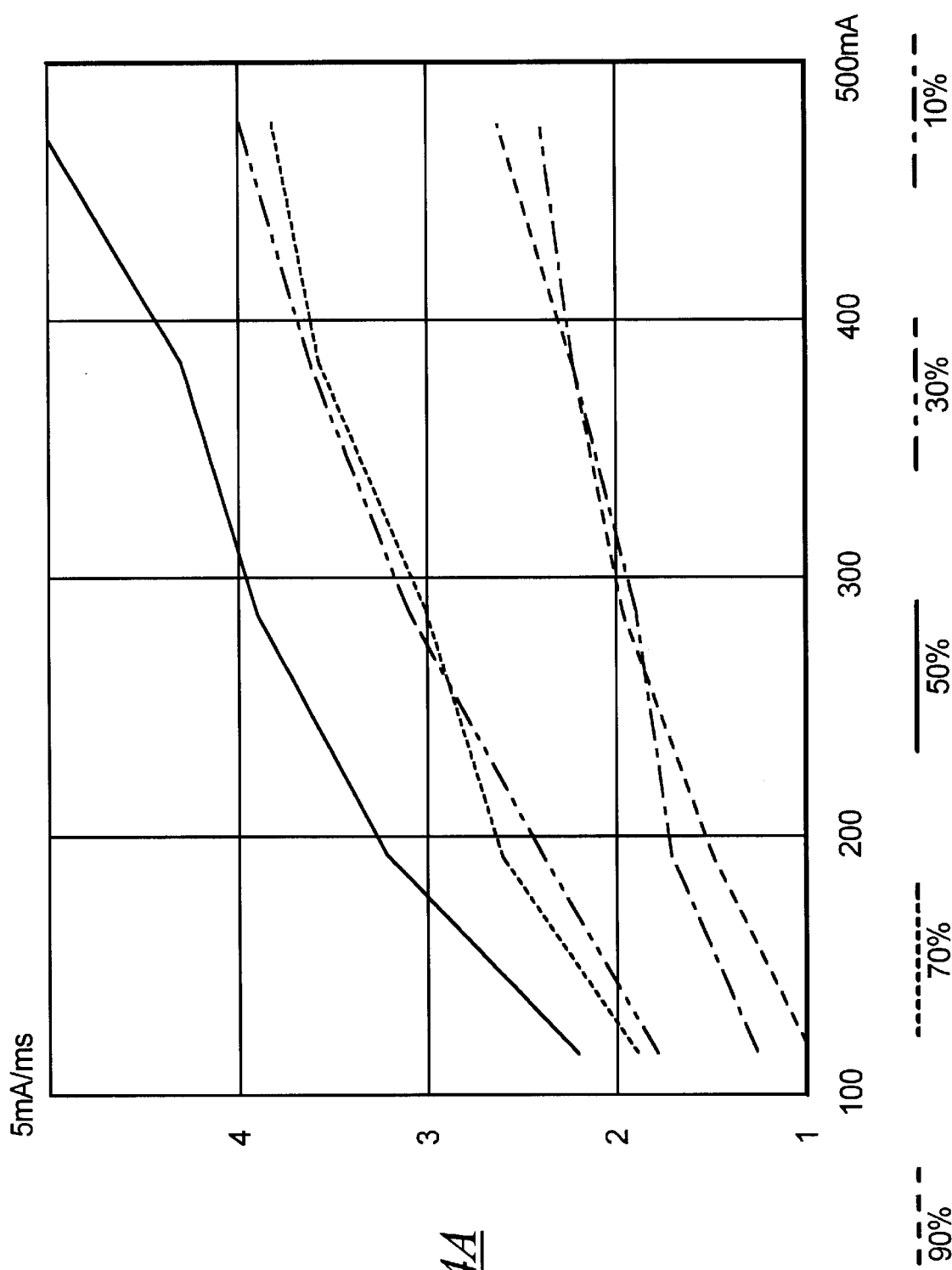
FIG. 4A shows the modulation speed for a large focus as a function of nominal current at 120 kV.
Figure 4B:
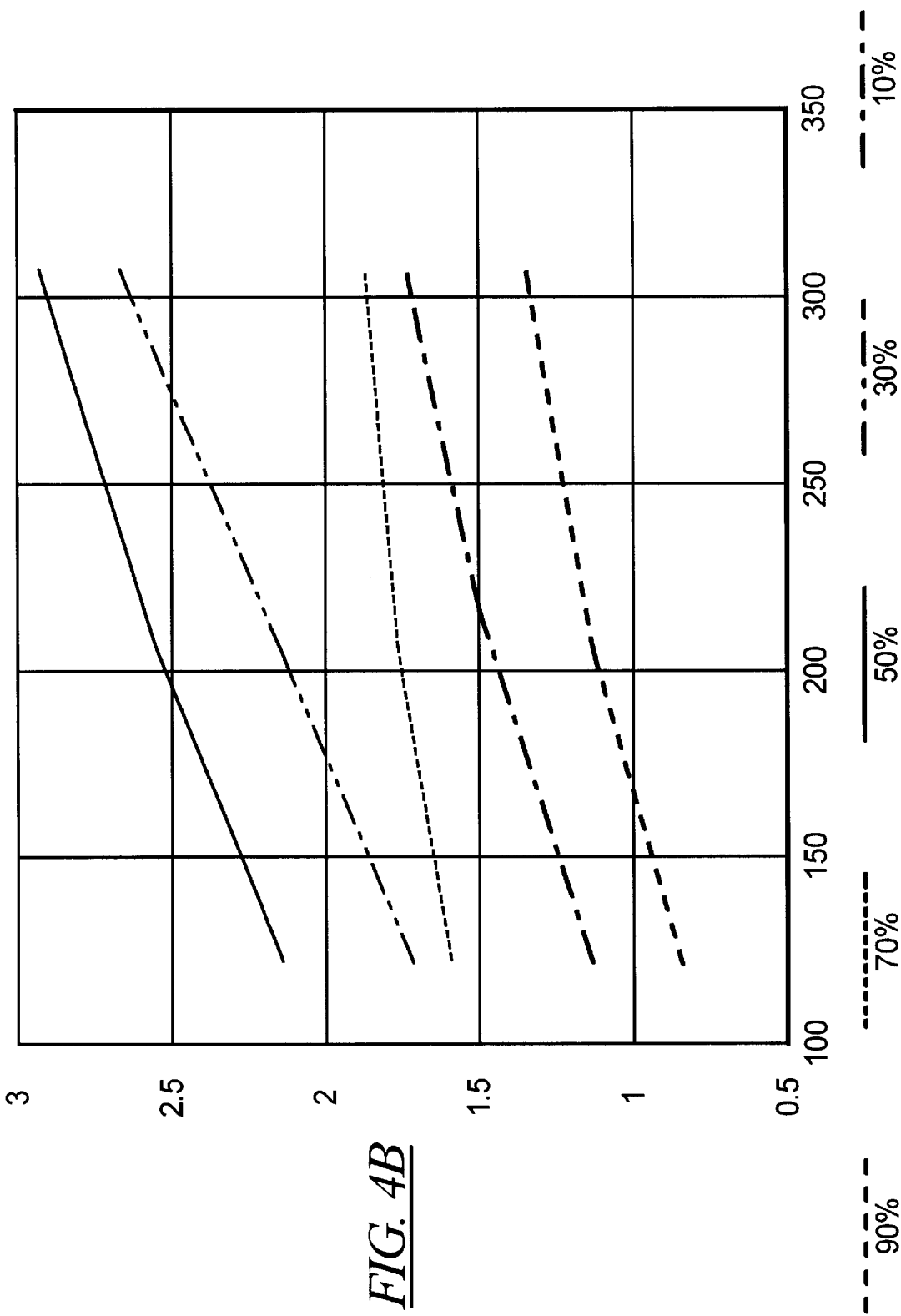
FIG. 4B shows the modulation speed for a small focus as a function of nominal current at 120 kV.

FIG. 1 shows the modulation speed for a large focus as a function of the nominal current at 120 kV, for a different modulation indices. The reason why the nominal current begins at 100 mA is because modulated scans with a current lower than this value are not possible, because the P20 x-ray radiator does not modulate the dose under such circumstances, and ignores the control signal, which would otherwise result in dose modulation, if the nominal current is lower than 100 mA. FIG. 4B shows the same situation for a small focus.

Figure 5A:
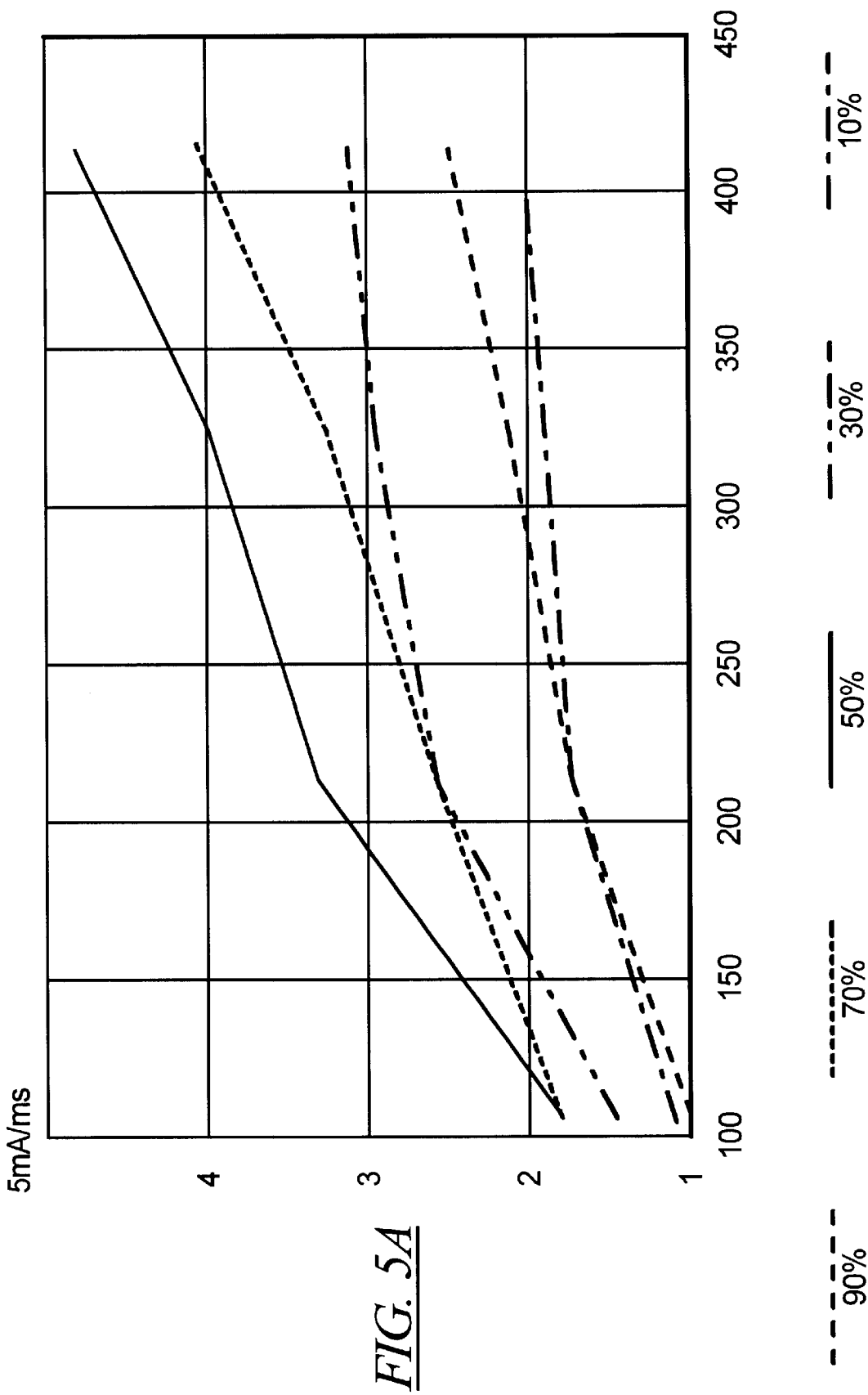
FIG. 5A shows the modulation speed for a large focus as a function of nominal current at 140 kV.
Figure 5B:
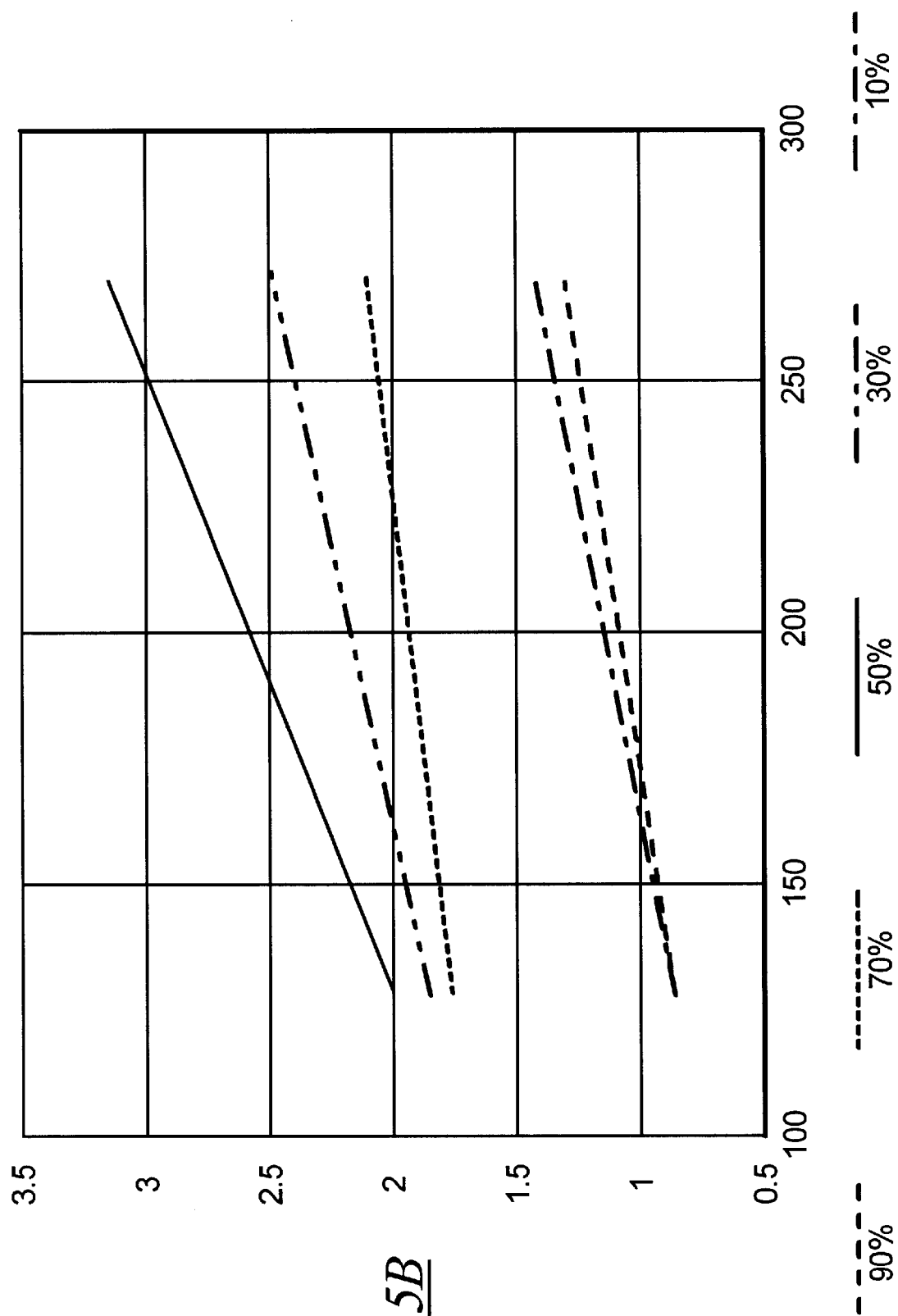
FIG. 5B shows the modulation speed for a small focus as a function of the modulation index.

FIG. 5A shows the modulation speed, at various modulation indices, for a large focus as a function of nominal current at 140 kV, and FIG. 5B shows the same situation for a small focus.

Figure 6A:
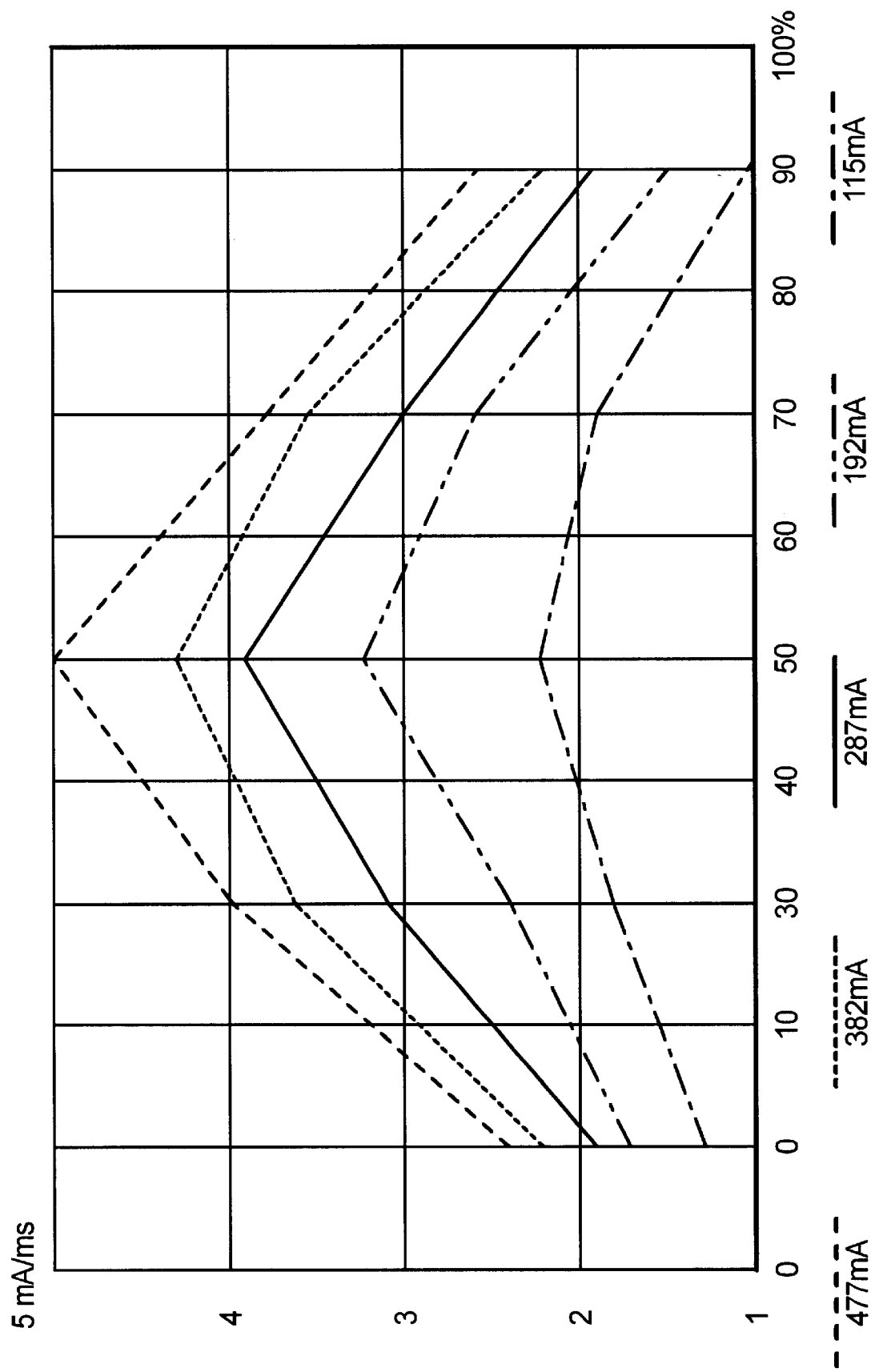
FIG. 6A shows the modulation speed for a large focus at 120 kV as a function of the modulation index.
Figure 6B:
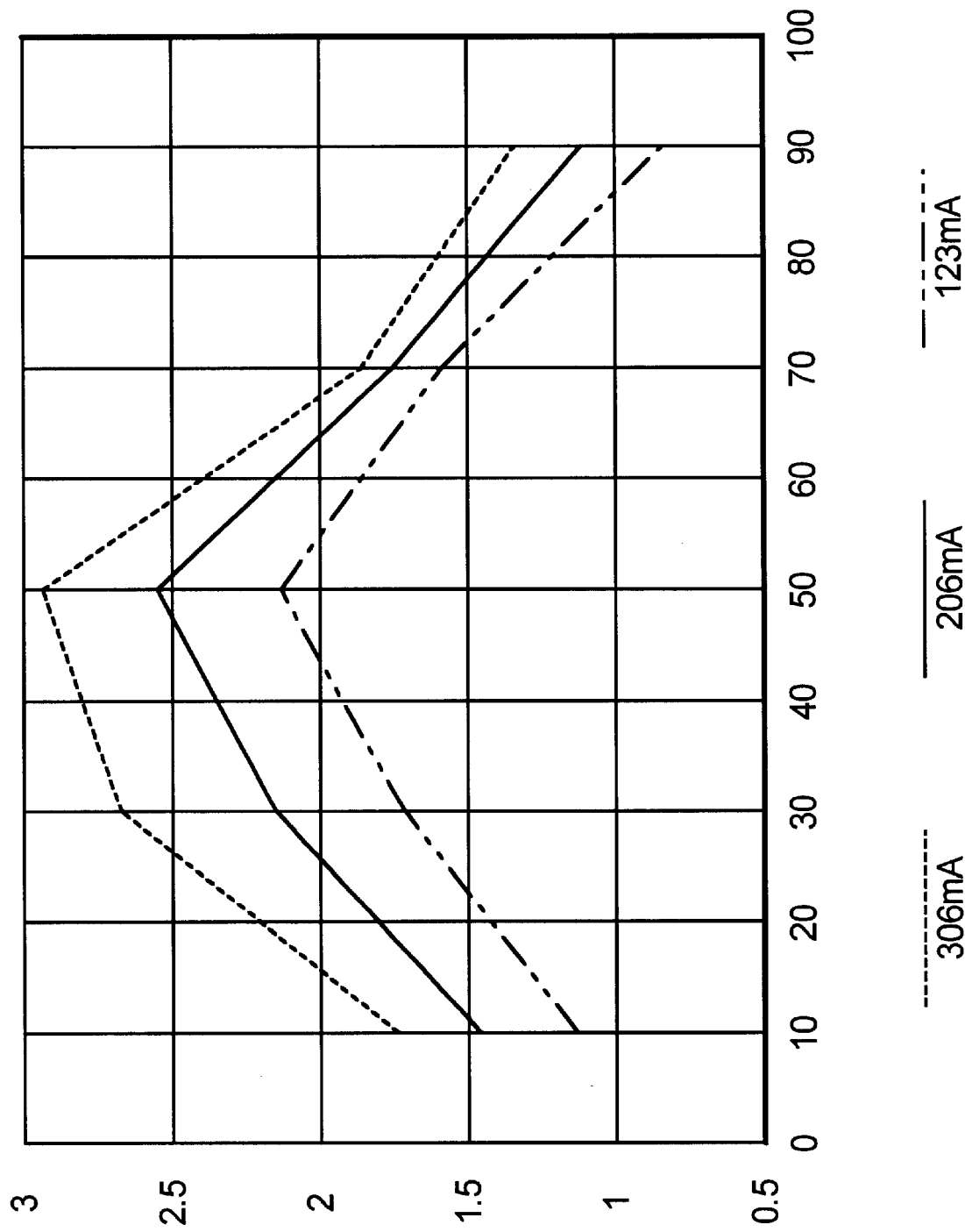
FIG. 6B shows the modulation speed for a small focus at 120 kV as a function of the modulation index.

FIGS. 6A and 6B demonstrate that the modulation speed depends non-linearly on the modulation index. The maximum modulation speed is achieved for a 50% modulation index, and the modulation speed decreases substantially linearly in the direction of larger or smaller modulation indices. The modulation speeds for 30% and 70% are almost equal, and the same is true for modulation speeds at 10% and 90%. FIG. 5A shows the modulation speed as a function of the modulation index for a large focus at 120 kV, and FIG. 6B shows the relationship under the same circumstances for a small focus. Investigations were also undertaken to show the relationship for a large and small focus at 140 kV. These relationships are similar in form to those shown in FIGS. 6A and 6B, but are not included herein.

Figure 7:
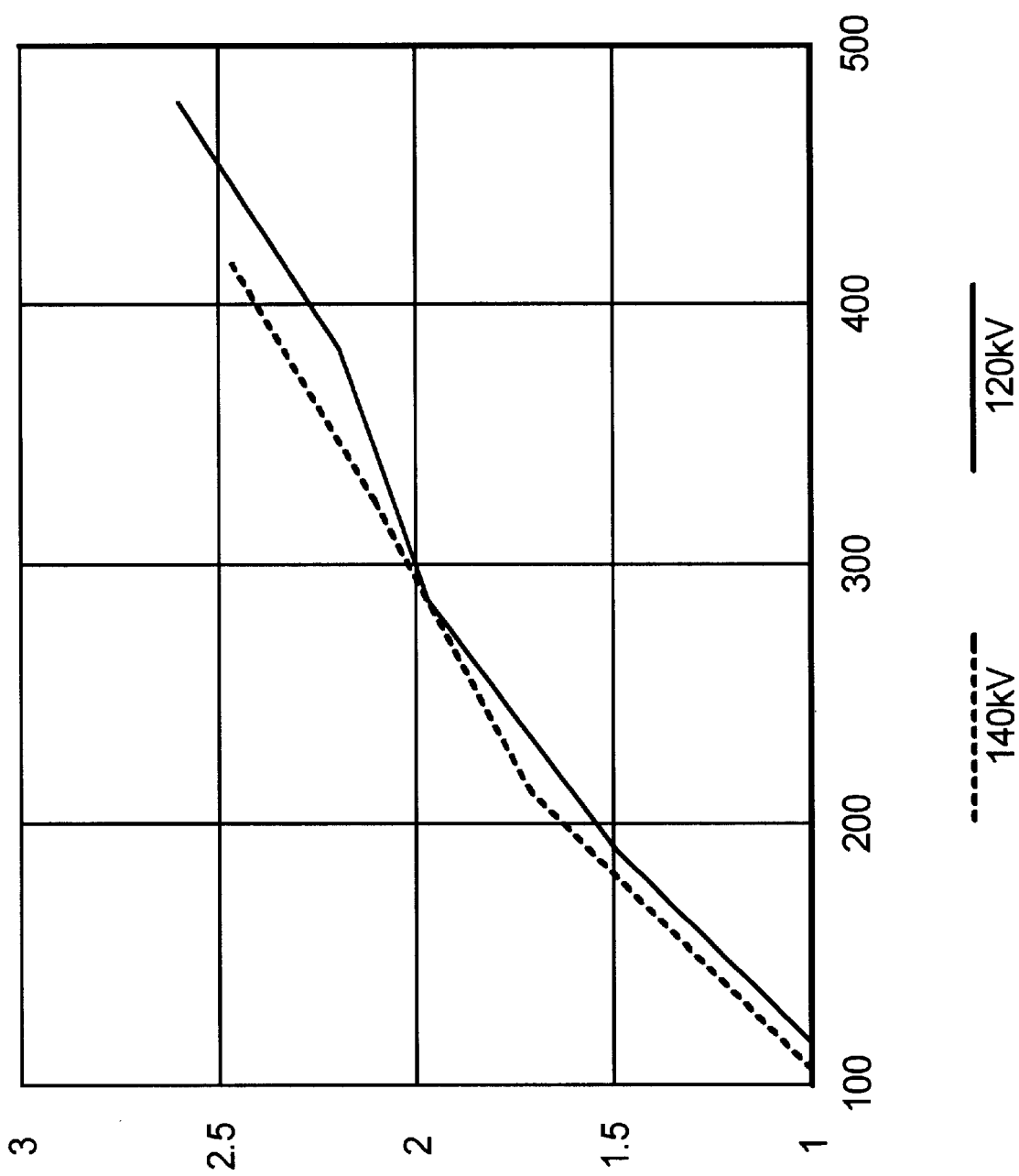
FIG. 7 shows the modulation speed for a large focus and 90% HUB (HUB =modulation index) at 120 kV and 140 kV.

FIG. 7 is a representative of the various investigations which were undertaken to determine the relationship, if any, of the modulation speed on the high voltage of the x-ray tube. As can be seen from FIG. 7, the modulation speed in the P20 x-ray radiator changes only slightly when the high voltage increases from 120 kV to 140 kV, and in fact the deviation shown in FIG. 7 is in a range which may be produced by measurement errors. FIG. 7 shows the modulation speed for a large focus and 90% HUB at 120 kV and 140 kV. Investigations were also undertaken for a large focus and 50% HUB at these voltages, a small focus and 90% HUB at these voltages, and a small focus and 50% HUB at these voltages. All of the results for these other investigations are similar to the results shown in FIG. 7.

Figure 8:
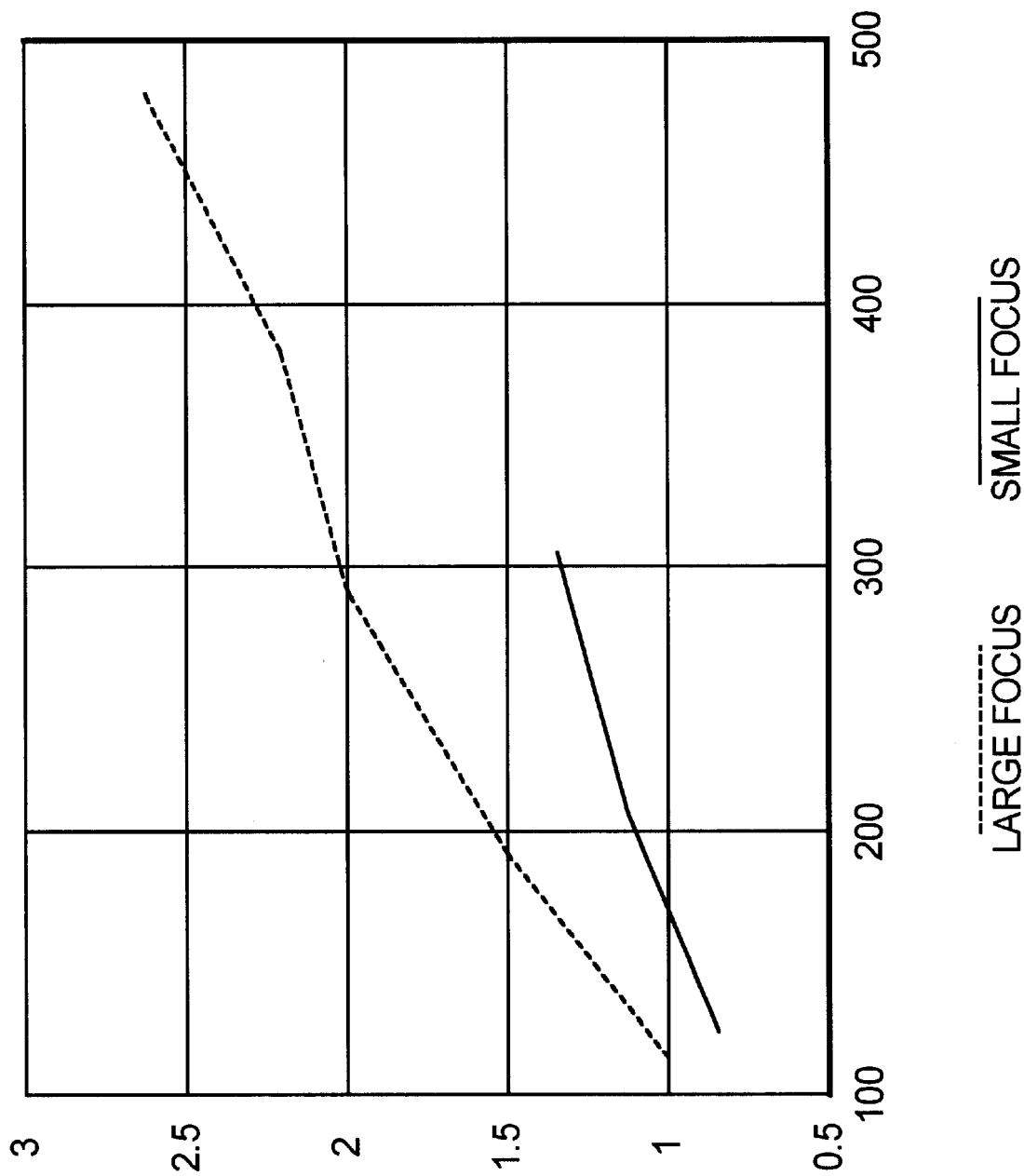
FIG. 8 shows the modulation speed for a large focus and for a small focus and 50% HUB at 120 kV.

FIG. 8 demonstrates that the modulation speed is dependent on focus size. FIG. 8 shows the modulation speed for a large focus and a small focus and 90% HUB at 120 kV. The same investigation was also undertaken for a large focus and a small focus at 50% HUB at 120 kV with results comparable to those shown in FIG. 8.

Typically a PID dose regulator is used in the tube current controller 11, and such a regulator has a predictable response only if the shape of the input control signal is exactly known. The above measurements were recorded when the P20 x-ray radiator was driven by a fast rectangular pulse signal, spanning the range between 10% and 100%. It is expected that for differently shaped control signals, the generator response will change.

The prediction of the generator response is a very complex undertaking, since a it involves two independent regulators, namely the regulator in the dose modulation unit 12 and the regulator in the tube current controller 11, each having a separate algorithm and operating parameters or configuration constants. Moreover, the variation of the modulation speed with the modulation index is extremely difficult to compensate using software. This would result in an iterative correction method, whereby the dose profile must be continuously adjusted until it reaches a stable modulation index and speed, for a modulation index that was not previously known. Due to time constraints, this is not practical for real time operation, and therefore an additional sacrifice in dose saving would have to be made in order to compensate for the slowness of the x-ray tube.

The modulation speed matrices, examples of which are shown below in Tables 1–4, offer a temporary solution to these problems, by overcompensating the x-ray tube speed. It is recognized, however, that as the rotational speed of future computed tomography systems increases, this overcompensation technique will eventually result in a dose reduction that is so small that the effort at compensation will not be justified. Nevertheless, for currently available CT systems employing conventional x-ray tubes, the inventive method and apparatus offer significant advantages.

TABLE 1

Modulation speed [mA/ms] for large focus at 120 kV

| HUB Itube[mA] | 90% | 70% | 50% | 30% | 10% |
|---|---|---|---|---|---|
| 477 | 2.60 | 3.80 | 5.00 | 3.97 | 2.38 |
| 382 | 2.20 | 3.56 | 4.30 | 3.60 | 2.20 |
| 287 | 1.97 | 3.00 | 3.90 | 3.07 | 1.90 |
| 192 | 1.50 | 2.60 | 3.20 | 2.40 | 1.70 |
| 115 | 1.00 | 1.90 | 2.20 | 1.80 | 1.28 |

TABLE 2

Modulation speed [mA/ms] for large focus at 140 kV

| HUB Itube[mA] | 90% | 70% | 50% | 30% | 10% |
|---|---|---|---|---|---|
| 500 | n.a. | n.a. | n.a. | n.a. | n.a |
| 414 | 2.46 | 4.00 | 4.80 | 3.10 | 2.00 |
| 324 | 2.10 | 3.24 | 3.98 | 2.95 | 1.90 |
| 214 | 1.70 | 2.56 | 3.29 | 2.56 | 1.70 |
| 107 | 1.00 | 1.80 | 1.80 | 1.46 | 1.10 |

TABLE 3

Modulation speed [mA/ms] for small focus at 120 kV

| HUB Itube[mA] | 90% | 70% | 50% | 30% | 10% |
|---|---|---|---|---|---|
| 500 | n.a. | n.a. | n.a. | n.a. | n.a. |
| 400 | n.a. | n.a. | n.a. | n.a. | n.a. |
| 306 | 1.34 | 1.86 | 2.94 | 2.67 | 1.73 |

TABLE 3-continued

Modulation speed [mA/ms] for small focus at 120 kV

| HUB Itube[mA] | 90% | 70% | 50% | 30% | 10% |
|---|---|---|---|---|---|
| 206 | 1.12 | 1.76 | 2.55 | 2.15 | 1.46 |
| 123 | 0.84 | 1.59 | 2.14 | 1.71 | 1.13 |

TABLE 4

Modulation speed [mA/ms] for small focus at 140 kv

| HUB Itube[mA] | 90% | 70% | 50% | 30% | 10% |
|---|---|---|---|---|---|
| 500 | n.a. | n.a. | n.a. | n.a. | n.a. |
| 400 | n.a. | n.a. | n.a. | n.a. | n.a. |
| 390 | n.a. | n.a. | n.a. | n.a. | n.a. |
| 270 | 1.30 | 2.10 | 3.14 | 2.48 | 1.42 |
| 129 | 0.88 | 1.77 | 2.00 | 1.86 | 0.86 |

Although modifications and changes may be suggested by those skilled in the art, intention of the inventor to embody within the patent warranted hereon all changes and modifications as reasonably and properly come within the scope of his contribution to the art.

I claim as my invention:

1. A method for modulating a radiation dose from an x-ray tube, comprising the steps of:
    (a) providing an x-ray tube having at least one variable operating parameter which, when varied, modulates a radiation dose, with a modulation speed, for x-rays produced by said x-ray tube;
    (b) operating said x-ray tube while varying said operating parameter through a parameter range and generating modulation speed data representing modulation speeds respectively for different values of said operating parameter;
    (c) identifying an exposure effect, associated with exposure of a subject to said radiation dose, that is dependent on modulation of said radiation dose; and
    (d) varying said operating parameter in advance of a time at which said exposure effect is to be achieved, according to said modulation speed data, to modulate said radiation dose while irradiating said subject with x-rays from said x-ray tube to produce said exposure effect at said time.

2. A method as claimed in claim 1 comprising selecting said at least one operating parameter from the group consisting of maximum tube current, focus size and modulation index.

3. A method as claimed in claim 1 wherein step (a) comprises providing an x-ray tube having a plurality of variable operating parameters which, when varied, modulate a radiation dose, with a modulation speed, for x-ray produced by said x-ray tube, and wherein step (b) comprises operating said x-ray tube while varying multiple operating parameters in said plurality of operating parameters through respective parameter ranges to generate modulation speed data representing modulation speeds respectively for different combinations of said multiple operating parameters, and wherein step (d) comprises varying said multiple operating parameters in advance of said time.

4. A method as claimed in claim 3 comprising selecting said multiple operating parameters from the group consisting of maximum tube current, focus size and modulation index.

5. A method as claimed in claim 1 wherein said exposure of said subject to said radiation dose in step (c) comprises rotating said x-ray tube on a gantry around said subject to expose said subject to x-rays from said x-ray tube at a plurality of successive projection angles in a computed tomography examination of said subject, and wherein step (a) comprises selecting said at least one variable operating parameter from the group consisting of maximum tube current, focus size, modulation index and projection angle.

6. A method as claimed in claim 5 wherein step (a) comprises providing an x-ray tube having a plurality of variable operating parameters which, when varied, modulate a radiation dose, with a modulation speed, for x-ray produced by said x-ray tube, and wherein step (b) comprises operating said x-ray tube while varying multiple operating parameters in said plurality of operating parameters through respective parameter ranges to generate modulation speed data representing modulation speeds respectively for different combinations of said multiple operating parameters, and wherein step (d) comprises varying said multiple operating parameters in advance of said time.

7. A method as claimed in claim 1 wherein said exposure effect in step (c) is minimization of quantum noise in an x-ray image obtained by said exposure of said subject to said radiation dose, and wherein step (d) comprises varying said operating parameter to produce substantial coincidence between a maximum intensity of said x-rays from said x-ray tube and a peak x-ray absorption of said subject.

8. A method as claimed in claim 1 wherein step (b) comprises operating said x-ray tube at multiple focus sizes, and varying said operating parameter through said parameter range for each of said multiple focus sizes, and generating said modulation speed data for each of said focus sizes.

9. A method as claimed in claim 1 wherein step (b) includes obtaining a nominal modulation profile for modulating said radiation dose, said nominal modulation profile having rising portions and falling portions, and employing said modulation speed data to modify only said rising portions of said modulation profile.

10. A computed tomography apparatus comprising:
    an x-ray tube having at least one variable operating parameter which, when varied, modulates a radiation dose, with a modulation speed, for x-rays produced by said x-ray tube;
    a radiation detector on which said x-rays are incident;
    a gantry on which said x-ray tube and said detector are mounted, said gantry being adapted for rotation around a subject to obtain image data representing said x-rays attenuated by said subject;
    an image computer supplied with said image data for reconstructing an image of said subject therefrom;
    a dose modulation unit containing modulation speed data obtained while operating said x-ray tube while varying said operating parameter through a parameter range, said modulation speed data representing modulation speeds respectively for different values of said operating parameter; and
    a controller connected to said x-ray tube and said dose modulation unit for operating said x-ray tube to produce an exposure effect, associated with exposure of a subject to said radiation dose, that is dependent on modulation of said radiation dose by varying said operating parameter in advance of a time at which said exposure effect is to be achieved, according to said modulation speed data, to modulate said radiation dose while irradiating said subject with x-rays from said x-ray tube to produce said exposure effect at said time.

11. A computed tomography apparatus as claimed in claim 10 wherein said at least one operating parameter is selected from the group consisting of maximum tube current, focus size and modulation index.

12. A computed tomography apparatus as claimed in claim 10 wherein said x-ray tube has a plurality of variable operating parameters which, when varied, modulate a radiation dose, with a modulation speed, for x-rays produced by said x-ray tube, and wherein said dose modulation unit contains modulation speed data obtained while operating said x-ray tube while varying multiple operating parameters in said plurality of operating parameters through respective parameter ranges, said modulation speed data representing modulation speeds respectively for different combinations of said multiple operating parameters, and wherein said controller varies said multiple operating parameters in advance of said time.

13. A computed tomography apparatus as claimed in claim 12 wherein said multiple operating parameters are selected from the group consisting of maximum tube current, focus size and modulation index.

14. A computed tomography apparatus as claimed in claim 10 wherein said gantry rotates said x-ray tube and said radiation detector around said subject to expose said subject to x-rays from said x-ray tube at a plurality of successive projection angles and wherein said at least one variable operating parameter is selected from the group consisting of maximum tube current, focus size, modulation index and projection angle.

15. A computed tomography apparatus as claimed in claim 14 wherein said x-ray tube has a plurality of variable operating parameters which, when varied, modulate a radiation dose, with a modulation speed, for x-rays produced by said x-ray tube, and wherein said dose modulation unit contains modulation speed data obtained while operating said x-ray tube while varying multiple operating parameters in said plurality of operating parameters through respective parameter ranges, said modulation speed data representing modulation speeds respectively for different combinations of said multiple operating parameters, and wherein said controller varies said multiple operating parameters in advance of said time.

16. A computed tomography apparatus as claimed in claim 10 wherein said exposure effect is minimization of quantum noise in said image data, and wherein said controller varies said operating parameter to produce substantial coincidence between a maximum intensity of said x-rays from said x-ray tube and a peak x-ray absorption of said subject.

17. A computed tomography apparatus as claimed in claim 10 wherein said x-ray tube is operable with multiple focus sizes, and wherein said dose modulation unit contains modulation speed data obtained while varying said operating parameter through said parameter range for each of said multiple focus sizes, and said modulation speed data including respective datasets for each of said focus sizes.

18. A computed tomography apparatus as claimed in claim 10 wherein said controller contains a nominal modulation profile for modulating said radiation dose, said nominal modulation profile having rising portions and falling portions, and wherein said dose modulation unit employs said modulation speed data to modify only said rising portions of said modulation profile.

* * * * *